United States Patent [19]

Vadas et al.

[11] 4,377,380
[45] Mar. 22, 1983

[54] DUAL PLUNGER DENTAL AMALGAM DISPENSER

[76] Inventors: Leslie Vadas, 134 Riviera Dr., Los Gatos, Calif. 95030; Bert M. Sabo, 19200 Bountiful Acres, Saratoga, Calif. 95070

[21] Appl. No.: 216,146

[22] Filed: Dec. 15, 1980

[51] Int. Cl.³ ............................................. A61C 5/04
[52] U.S. Cl. ..................................... 433/89; 222/391
[58] Field of Search ............... 433/89, 83, 90, 80; 222/252, 253, 256, 391, 340; 141/249, 386

[56] References Cited

U.S. PATENT DOCUMENTS

| | | | |
|---|---|---|---|
| 1,706,060 | 3/1929 | Hakins | 433/90 |
| 2,648,906 | 8/1953 | Holmes | 433/90 |
| 3,280,459 | 10/1966 | Walher et al. | 32/60 |
| 3,322,307 | 5/1967 | Fraser | 423/90 |
| 3,537,617 | 11/1970 | Mendola | 433/83 |
| 3,623,224 | 11/1971 | Smith | 32/60 |
| 3,638,314 | 2/1972 | Lopez | 32/60 |
| 3,751,807 | 8/1973 | Noll | 32/60 |
| 3,792,530 | 2/1974 | Smith | 433/83 |
| 3,965,578 | 6/1976 | Warden et al. | 433/83 |
| 4,173,236 | 11/1979 | Hirder | 433/89 |

FOREIGN PATENT DOCUMENTS

| | | | |
|---|---|---|---|
| 402649 | 9/1924 | Fed. Rep. of Germany | 433/90 |
| 30933 | 5/1929 | United Kingdom | 433/89 |

*Primary Examiner*—Gene Mancene
*Assistant Examiner*—John J. Wilson
*Attorney, Agent, or Firm*—C. E. Tripp

[57] ABSTRACT

A dental amalgam dispensing instrument has an amalgam dispensing head having a dispensing passage slidably receives a rectangular section dispensing passage with an amalgam feed passage intersecting the dispensing passage. A straight rectangular section feed plunger slides in the feed passage and is slidably carried by a handle that is detachably mounted on the head. The dispensing passage in the head is formed as an elongate channel opening toward the front of the instrument and a detachable cover plate closes the front of the channel.

19 Claims, 16 Drawing Figures

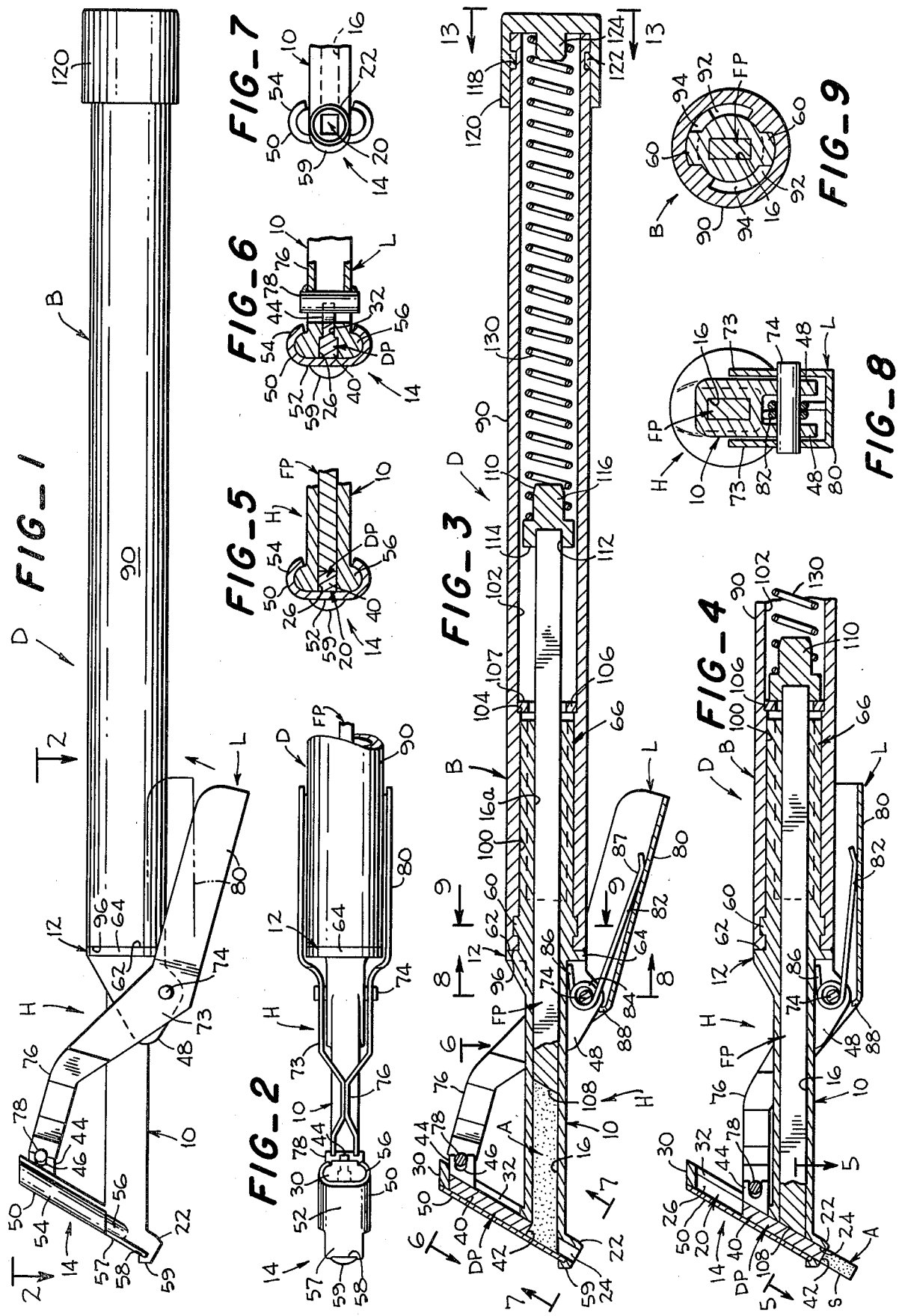

U.S. Patent  Mar. 22, 1983  Sheet 2 of 2  4,377,380
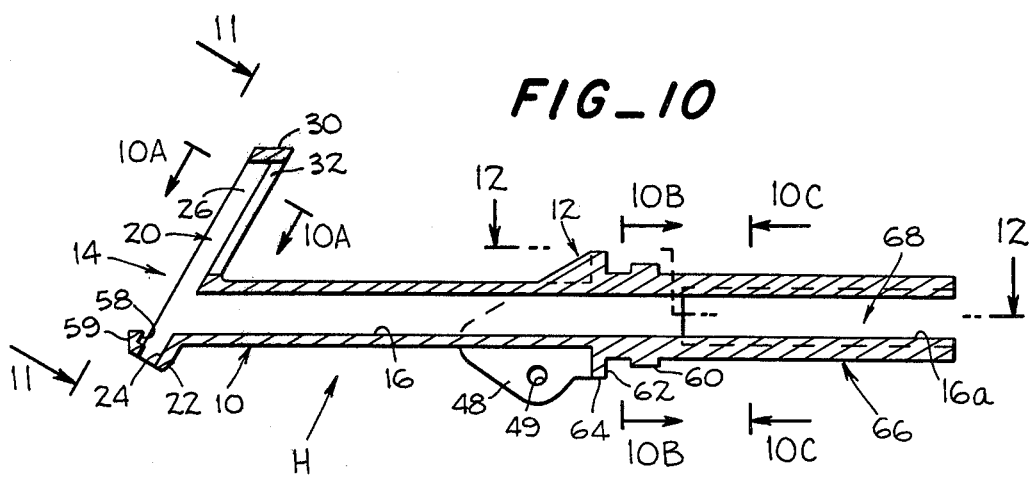
FIG_10
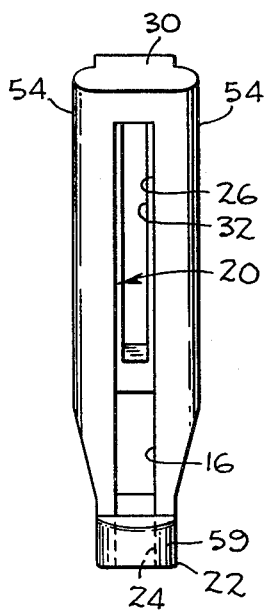
FIG_11
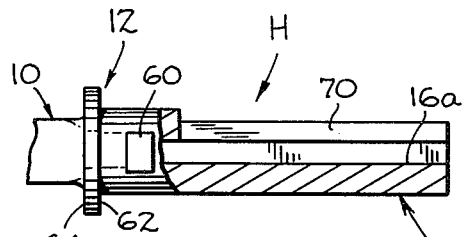
FIG_10A  FIG_10B  FIG_10C
FIG_12
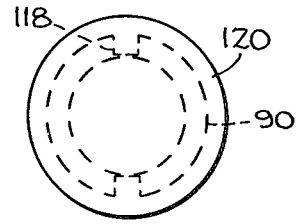
FIG_13

DUAL PLUNGER DENTAL AMALGAM DISPENSER

FIELD OF THE INVENTION

This invention relates to dental amalgam dispensing instruments and more particularly to a dispenser of the dual plunger type.

SUMMARY OF THE INVENTION

A known form of dental amalgam dispensing instrument for filling tooth cavities includes a dispensing head element having a dispensing passage that receives a dispensing plunger. The head element has a handle element and the instrument is formed with an amalgam feed passage having a forward end that intersects the dispensing passage. The feed passage is loaded with amalgam and a feed plunger is advanced in the feed passage to feed amalgam to the dispensing passage, whereupon the dispensing plunger is advanced to discharge amalgam from the head for filling a cavity.

One problem that arises during the use of such instruments resides in clearing the head of amalgam after use, particularly at the intersection of the feed passage with the dispensing passage. In accordance with the present invention, the feed plunger has a front end face that is shaped to form a continuation of the rear wall of the dispensing passage. With this construction, when the instrument is to be cleared of amalgam, the dispensing plunger is repeatedly advanced and retracted until the feed plunger is fully advanced. At this time, a final advance of the dispensing plunger clears the passage intersection and the dispensing and feed passages are cleared of amalgam. More specifically, the front end face of the feed plunger is shaped to form a continuation of the rear wall of the dispensing passage, and hence the aforesaid amalgam clearing operation completely clears the zone of passage intersection of amalgam, leaving no amalgam in corners or pockets.

In the preferred embodiment of invention, both the dispensing and feed passages are rectangular in cross section, or at least the rear wall of the dispensing passage is planar and the front end face of the dispensing plunger is flat so that the front end face of the feed plunger and the dispensing passage wall are both planar. This construction provides for automatic clearing of the passage intersection by operation of the dispensing plunger.

In the preferred embodiment of the invention, a stop is provided which limits advance of the feed plunger to the aforesaid position wherein the front end face of the feed plunger is "flush" with the rear wall of the dispensing passage.

In order to facilitate manual clearing of any small amalgam particles that may remain in the head, the dispensing head passage is formed to provide an elongate channel opening toward the front of the instrument to provide direct access to the head passages for manual cleaning. Preferably, the head includes keepers such as ribs at each side of the channel and a cover plate for the channel is provided that has side flanges for embracing the keepers. Removal of the cover plate provides the aforesaid direct access to the passages for cleaning.

In order to prevent deflection of the cover plate under the force of amalgam being advanced by the feed plunger, the tip portion of the head is formed with a socket that receives an associated end portion of the cover plate.

Another feature of the preferred embodiment of the invention is that although the feed passage is formed entirely in the head, the feed plunger is mounted in the handle and remains in the handle when the head is removed from the handle. This further facilitates cleaning of the feed passage by providing access thereto from both ends of the passage.

The feed plunger is a straight rigid bar, preferably of rectangular cross section and can rotate in the handle during mounting of the head. In the preferred embodiment of the invention, the feed plunger is advanced by a coil spring that is confined in the handle. A stop in the handle limits advance of the feed plunger to its position wherein the front face of the plunger is "flush" with the rear wall of the dispensing passage in the head when the plunger is fully advanced. The feed plunger can be withdrawn from the handle by moving an end cap for the handle.

In order to facilitate manual loading of the feed passage in the head with amalgam before the head is attached to the handle, the rear or breech portion of the head has a rearward extension. This extension is formed with a three sided channel that forms a continuation of the feed passage. A diverging wall opening or "funnel" opens into the channel for receiving charges of amalgam for the feed passage of the head before the head is attached to the handle. The amalgam is then pushed into the feed passage using a simple blade or tool.

The manner in which these and other features and advantages are attainable will be apparent to those skilled in the art in the follwing detailed description of the embodiment of the invention.

IN THE DRAWINGS

FIG. 1 is a side view of the instrument with the actuator shown retracted in full lines.

FIG. 2 is a partial plan view looking along line 2—2 of FIG. 1.

FIG. 3 is a longitudinal vertical section through the instrument with the actuator retracted.

FIG. 4 is a partial section like that of FIG. 3 with actuator depressed and showing the amalgam clearing action.

FIG. 5 is a section taken on line 5—5 of FIG. 4.

FIG. 6 is a section taken on line 6—6 of FIG. 3.

FIG. 7 is a bottom view of the head looking along line 7—7 of FIG. 3.

FIG. 8 is a section taken on line 8—8 of FIG. 3.

FIG. 9 is a section taken on line 9—9 of FIG. 3.

FIG. 10 is a vertical section through the head with all parts removed.

FIG. 10A is a section through the dispensing portion of the head taken on line 10A—10A of FIG. 10

FIG. 10B is a section through the breech of the head taken on line 10B—10B of FIG. 10.

FIG. 10C is a section through the loading extension of the head taken on line 10C—10C of FIG. 10.

FIG. 11 is a front view of the dispensing end of the head looking along line 11—11 of FIG. 10.

FIG. 12 is a partial section of the rear portion of the head looking along line 12—12 of FIG. 10.

FIG. 13 is a rear end view of the instrument looking alone line 13—13 of FIG. 3.

DETAILED DESCRIPTION

General Arrangement

Referring to FIGS. 1–3, a dispensing instrument D embodying the invention includes a discharge or dispensing head H (hereinafter referred to as the "head") which is quickly attachable to a body or handle B by a bayonet joint connection. A manually actuated dispensing plunger DP slides in the head H (FIG. 3) and a spring loaded feed plunger FP is mounted in the handle B and projects into the head. By successfully squeezing or actuating an actuator L, the dentist causes the dispensing plunger DP to discharge slugs of amalgam A (FIG. 4) from the tip of head H for filling the tooth cap. The feed plunger FP is automatically advanced by a spring on the handle.

The Head

Referring to FIGS. 3–12, the head H includes a longitudinal tube 10 having a rearward breech portion 12 forming part of a bayonet joint connection with the handle B. The front of the head includes a short amalgam dispensing tip 14 that is inclined at an acute angle to the axis of tube 10. Tube 10 is formed with a full length, rectangular section amalgam feed passage 16 that receives the front end of the feed plunger FP and that intersects an amalgam dispensing passage, indicated generally at 20, formed in the tip 14.

The discharge end 24 of the amalgam dispensing passage 20 extends through a short discharge nozzle 22 forming the lower end of tip 14 and projecting from the tube 10. As seen in FIG. 7, the nozzle portion of the dispensing passage 20 is a full rectangle in section, the rectangle preferably being a square. As thus seen in FIGS. 10, 10A and 11, the majority of the dispensing passage 20 is formed as a front opening channel 26 that forms two sides and the rear wall of the full section square nozzle passage 24. The channel 26 receives the dispensing plunger DP. The end of channel 26 remote from the nozzle passage 24 (the upper end) is closed by an end cap 30 that is integral with the tip 14.

In order to slidingly receive an operating ear on the dispensing plunger DP (FIG. 3) and as seen in FIGS. 3, 6, 10, 10A and 11, the upper portion of the tip 14 is rearwardly slotted at 32, the slot extending between the tube 10 and the end cap 30.

Referring to FIGS. 3, 4 and 6, the dispensing plunger DP has an elongate square-section plunger portion 40, slidably received in the channel portion 26 of the dispensing passage 20. The plunger portion 40 has a lower end face 42 (FIGS. 3 and 4) for shearing off slugs of amalgam A at the intersection of the dispensing passage 20 with the feed passage 16. In order to provide for reciprocation of the dispensing plunger DP, an actuating ear 44 projects rearwardly from the upper end of plunger portion 40 and the ear is slotted at 46 for receiving an actuator pin on the front pin of the actuator L. The ear 44 slides in the slot 32, previously described.

In order to pivotally mount the actuator L, the tube 10 has depending ears 48 (FIGS. 3 and 8 and 10C) that are apertured at 49 for receiving an actuator pivot pin.

As seen in FIGS. 1–7, in order to provide access to the dispensing passage 20 and the feed passage 16 for cleaning and to provide for fitting the dispensing plunger DP into the channel 26, the front side of the channel 26 is closed by a removable cover plate 50. The cover plate has a flat front portion 52 that extends along its length and closes off the channel 26 in the tip 14 to complete the dispensing passage 20 along the full length of the tip 14.

The cover plate 50 is retained on the tip 14 by laterally spaced channel flanges 54 that embrace half-round keeper ribs 56 projecting from the sides of the tip 14. Deflection of the lower end of cover plate 50 under forces exerted by the amalgam A during operation is prevented by confining the lower end portion 57 of the cover plate in a notch 58 formed in a boss 59 (FIGS. 1, 3, 4, 10 and 10A) projecting forwardly from the tip nozzle 22.

The rearward or breech portion 12 of the head H is best seen in FIGS. 9–12 and includes a bayonet joint element for quick connection to the handle B and an amalgam loading element. The bayonet joint element is formed by opposed lugs 60 projecting from the breech portion 12 and a rearwardly facing locating shoulder 62 formed on a flange 64. These elements cooperate with companion bayonet joint elements formed at the front of the handle B.

The loading element of the breech portion 12 of the head is a construction which facilitates manual loading of pre-mixed amalgam into the feed passage 16 before the head is attached to the handle B. The breech portion of the head has a loading extension 66 projecting rearwardly from the bayonet joint element 12. The extension is formed with a three sided loading channel 16a (FIGS. 3, 10 and 10C). This forms a rearward continuation of the feed passage 16. As best seen in FIGS. 10, 10C and 12, access to the channel 16 is provided from one side and along its length by a loading slot 68 formed in the extension 66 and having diverging walls 70.

When the head is detached from the handle, premixed amalgam is loaded into the loading channel 16a through the loading slot 68, the diverging walls 70 acting as a funnel. Preferably, the pre-mixed amalgam is dispensed as one or more discrete slugs or panels by a combined mixer and dispenser unit known in the art. The resultant charge or charges of amalgam in the channel 16a are then manually pushed forwardly into the feed passage 16 by a suitably shaped pushing tool or paddle (not shown). The loaded head H can now be attached to the handle by sliding the feed plunger FP along the loading channel 16a, and into the feed passage 16, and making a connection with the actuator, to be described. By inserting the bayonet joint element lugs 60 into suitable slots formed in the handle forming a companion bayonet joint on the handle and rotating the head on the handle, the instrument is ready for use.

Actuator

The actuator L is pivotably mounted on the head H and provides for manual advance of the dispensing plunger DP for dispensing slugs "s" (FIG. 4) of amalgam A from the discharge end 24 of the dispensing passage 20. The mid-portion of the actuator is formed with flanges 73 (FIG. 2) that straddle the ears 48 on the head and are pivotally mounted on the ears by a pin 74 which extends through the apertures 49 (FIG. 10) in the ears. The flanges 73 on the actuator are shaped to straddle the tube 10 on the head H and form a front arm 76 (FIGS. 1–4). The front end of actuator arm 76 is welded to a short pin 78 that fits in the slot 46 formed in the ear 44 on the upper end of the dispensing plunger DP.

The actuator has a rearwardly projecting arm 80 that is U-shaped in section and is disposed below the head H and the handle B (when attached) for operation by the dentist. A wire spring 82 has a coil portion 84 (FIG. 3) that surrounds the pin 74, a short leg 86 that engages the tube 10 of the head and a longer leg 87 that engages the actuator arm 80. The spring 82 urges the actuator to the position shown in full lines of FIG. 1, wherein the dispensing plunger DP is fully retracted with its upper end at the cap plate 30. At this position, a portion 88 of the actuator engages a stop surface formed on the underside of ears 48 on the head H (FIG. 3). When the actuator arm 80 is squeezed by the dentist to the position shown in FIG. 4, the dispensing plunger DP is advanced and a slug "s" of amalgam A is ejected from the head.

Handle

The body or handle B carries the feed plunger FP except when the parts are disassembled for cleaning or sterilization. The handle is formed as an elongate tube 90 (FIGS. 1-4), the front end of which is formed to provide a bayonet joint connection with the bayonet joint element on the breech portion 12 of the head H. As seen in FIG. 9, the handle has short axial grooves 92 that initially receive the lugs 60 on the breech 12 of the head during attachment of the head. Short circumferential grooves 94 intersect the axial grooves 92 for receiving the lugs 60 on the head during rotation of the head on the handle. A front end face 96 on the handle engages the rearwardly facing stop face 62 on the head.

As seen in FIG. 3, the loading extension 66 fits a bore 100 formed at the front portion of the handle B. The bore 100 joins a longer bore 102 of slightly greater internal diameter. The junction of bores 100 and 102 provide a small shoulder 104 that serves as a seat for a stop washer 106 which is pressed into the bore 102. The washer has a rearwardly facing stop face 107.

As seen in FIGS. 3 and 4, the front end of the feed plunger FP is beveled to form a flat front end face 108 that is inclined to the axis of handle B at the same angle of inclination as that of the dispensing passage 20 in the head. When the fixed plunger is fully advanced, the front end face 108 is "flush" with the rear wall of the dispensing passage 20 in the head and thus forms a continuation of the rear passage wall. As seen in FIG. 5, when the rear wall of the dispensing passage is flat, so is the front end face of the feed plunger FP. Thus, advance of the dispensing plunger DP, with the feed plunger fully advanced, clears the intersection of the feed passage 16 with the dispensing passage 20 of amalgam.

In order to limit advance of the feed plunger FP to the aforesaid "flush" position of the front end face 108, the rear end of the plunger is fitted with a combined stop collar and spring seat 110. The front side of the collar 110 is formed with a rectangular section socket 112 which receives the rear end of the rectangular section feed plunger FP with a press fit. A front face 114 of the collar serves as a stop face for engaging the rearwardly facing stop face 107 on the washer 106 that has been pressed into the bore 102 of the handle B. This engagement takes place when the feed plunger FP is fully advanced, as shown in FIG. 4. The aforesaid stop construction insures that the front end face 108 of the feed plunger will be "flush" with the dispensing passage rear wall, as previously described. The rear side of collar 110 is formed with a circular section spring centering post 116.

The rear end of the handle B (FIG. 3) is formed with a bayonet joint slot structure 118 to form a bayonet joint connection with an end closure cap 120. The cap 120 has bayonet joint lugs 122 that detachably retain the cap on the handle in the manner of the bayonet joint structure that secures the head H to the handle. A spring centering post 124 projects forwardly from the end wall of cap 120.

In order to urge the feed plunger FP toward its advanced position, and thus force amalgam A in the feed passage 16 (FIG. 4) into the intersection of that passage with the dispensing passage 20, a long coil spring 130 is contained within the bore 102 of the handle B. The front end of the spring 130 surrounds the post 116 on the feed plunger collar 110 and the rear end of the spring surrounds the spring post 124 on the end cap 120.

When the end cap is removed, the coil spring 130 and the feed plunger FP can be withdrawn from the handle through the rear end of the handle bore 102. This facilitates cleaning and sterilization of all handle parts.

Operation

Assume that the head H has been removed from the handle B. If the dispensing plunger DP has been removed for cleaning the feed passage 20 and dispensing passage 16 in the head, the dispensing plunger is mounted in the head by inserting the lower end thereof into the channel 26 forming a portion of the dispensing passage 20 and swinging the ear 44 rearwardly through the slot 32 along the rear wall of the dispensing passage. The dispensing plunger is positioned so that the slot 46 in the ear 44 slides over the pin 78 at the front end of the actuator A. The cover plate 50 is fitted by sliding its flanges 54 along the ribs 56 formed on the head until a lower end 57 of the plate slides into the notch 58 formed in the boss 59 at the lower tip or nozzle 22 of the head. The closure plate 50 will now withstand force exerted by the advance of amalgam A during operation of the instrument, without spring or deflection.

The desired amount of amalgam is now deposited into the open sided loading channel 16a (FIGS. 10, 10C and 12) which loading action is facilitated by the funnel provided by the diverging side walls 70 of the loading channel. The amount of amalgam that is deposited in the loading channel depends upon the size and the number of cavities to be filled. After the loading channel is charged with amalgam, the amalgam is pushed forwardly into the feed passage 16 by the use of a suitable tool or paddle (not shown), as previously described. The head H, now charged and loaded with amalgam A, is attached to the handle B utilizing the bayonet joint connections previously described in detail.

When the head H is partially turned as it is attached to the handle B, the feed plunger FP projects into the feed passage 16 formed in the head as seen in FIG. 3 and rotates with the head. The front face 108 of the feed plunger FP is brought against or in the vicinity of the rearward face of the body of amalgam A that was previously loaded into the feed passage in the head, as just described.

In order to dispense a slug "s" of amalgam A from the tip 22 of the head and into a tooth cavity (not shown) the dentist squeezes the actuator arm 80 bringing it adjacent the handle B as shown in FIG. 4, as well as in dotted lines in FIG. 1. This advances the dispensing plunger DP and shears off a body of amalgam at the intersection of the dispensing passage 20 with the feed passage 16. After dispensing plunger DP shears off the aforesaid body of amalgam at the passage intersection, continued advance of the plunger ejects a slug "s" from the tip 22 of the head as shown in FIG. 4. Of course, this slug "s" of amalgam is ejected into a tooth cavity during the filling operation.

When the actuator A is released by the dentist, the spring 82 returns the handle to its initial position shown in full lines in FIGS. 1 and 3. This retracts the dispensing plunger DP to the position shown in FIG. 3 with the upper end of the plunger engaging the end cap 30. The coil spring 130, acting against the rearward end of the feed plunger FP, now advances the feed plunger and forces the body of amalgam A in the feed passage 16 forwardly. The intersection of the feed passage 16 and the dispensing passage 20 is again filled with amalgam. If more amalgam is required to complete the tooth cavity filling operation or if another tooth is to be filled, the actuator A is squeezed as before, whereupon the dispensing plunger DP ejects a second slug "s" of amalgam from the tip 22 of the head into the cavity. The aforesaid amalgam dispensing action is repeated until the cavity or cavities are suitably filled with amalgam.

After the cavity filling operations have been completed, the head is mechanically cleared of all amalgam (assuming that amalgam still remains in the head). This clearing action is accomplished by repeatedly squeezing the handle with consequent advance and retraction of the dispensing plunger DP. Each advance of the dispensing plunger shears off a body of amalgam at the feed and dispensing passage intersection and ejects it from the nozzle and this action is continued until the coil spring 130 has urged the feed plunger FP to the fully advanced position shown in FIG. 4, wherein its stop collar face 114 engages the stop face 107 on the handle washer 106.

When the feed plunger attains its fully advanced position, subsequent advance of the dispensing plunger DP by actuation of the actuator handle ejects all the amalgam from the dispensing passage formed in the head of the instrument. The intersection between the feed and dispensing passages is completely cleared of amalgam because the front face 108 of the feed plunger, the side walls of the channel 26 that forms a portion of the dispensing passage and the inside wall of the closure plate 50 form a rectangular section passage (preferably a square section passage) which is filled by the rectangular section dispensing plunger DP as it passes through the aforesaid passage intersection. This construction insures that the intersection will be cleared of amalgam by the dispensing plunger DP and since the dispensing plunger has a close fit with the feed passage, the nozzle passage 24 is also cleared of amalgam.

If it is desired to manually clean the amalgam passages, or to sterilize the instrument, the head H is removed from the handle by giving the head a partial turn on the handle. The end plate 50 is slid off the head and the dispensing plunger DP is removed from the open front dispensing passage channel 26. This gives ready access to the dispensing passage 20 as well as to the feed passage 16, which is now open at both ends. Any minute particles of amalgam that may have been left in the head can now be readily scraped out with a dental pick or the like.

As to materials of construction, it is preferred that the head H, the dispensing plunger DP, the feed plunger FP and the stop collar 110 be made as investment castings from stainless steel. The materials employed in the construction of the other elements of the instrument are of minor importance, although the body of the handle B and the end cap 120 can be molded from a tough thermo-setting plastic material.

In the appended claims, the statement that the front end face of the feed plunger forms a continuation of the rear wall of the dispensing passage, when the feed plunger is fully advanced, is intended to define structure having the mode of operation shown in FIGS. 4 and 5. Both the feed plunger and face and the dispensing passage rear wall are complimentary in cross-sectional contour, so that when the feed plunger is fully advanced, a dispensing passage is formed at the passage intersection that is fully occupied by the dispensing plunger, when the latter is advanced. This renders the instrument self-clearing.

In the preferred embodiment illustrated, this self-clearing action is attained by a construction wherein both the rear wall of the dispensing passage and the front end face of the feed plunger are planar, or flat.

In the claims, the term "rectangular" is used in its generic geometric sense and hence includes that special rectangle, the square.

Although the best mode contemplated for carrying out the present invention has been herein shown and described, it will be apparent that modification and variation may be made without departing from what is regarded to be the subject matter of the invention as defined in the appended claims.

What we claim is:

1. A dental amalgam dispensing instrument of the type having a dispensing head, said head comprising an elongate tube mounting an angularly disposed dispensing tip on the front end of said tube for introduction into an oral cavity, said tip being formed with a dispensing passage, a dispensing plunger that slidably fits the passage, an elongate hollow handle for the tube, actuator means for the dispensing plunger, said tube having an amalgam feed passage intersecting the dispensing passage, a feed plunger sliding in said feed passage and means for advancing said feed plunger; the improvement wherein said feed passage lies wholly within said tube, means for detachably mounting the rear end of said tube on said handle, said dispensing passage having an elongate planar rear wall and side walls that intersect said planar rear wall at an angle of about 90 degrees, said feed plunger having a planar front end face that forms a continuation of the planar rear wall of said dispensing passage when the feed plunger is fully advanced, said dispensing plunger having a planar rear surface that is laterally co-extensive with said planar rear wall of said dispensing passage so that advance of said dispensing plunger, when the feed plunger is fully advanced, clears the passage intersection of amalgam, a feed plunger stop member projecting into the hollow of said handle, a stop abutment on said feed plunger disposed entirely within the hollow of said handle for engaging said stop member in the handle and for limiting advance of said feed plunger to a position wherein its front end face is flush with the rear wall of said dispensing passage, and a spring in said handle for advancing said feed plunger, said feed plunger being withdrawn from said head by said stop member upon detachment of the head from the handle.

2. The instrument of claim 1; wherein said dispensing and feed passages and their respective plungers are of rectangular shape in cross-section, said feed plunger being a straight, elongate rigid bar of uniform rectangular cross-section along substantially its entire length, as measured along the axis of said elongate handle, said rectangular cross-section having a major axis parallel to the axis of said dispensing passage, said stop abutment being mounted at the rear of said bar.

3. A dental amalgam dispensing instrument of the type having a dispensing head formed with a dispensing passage that slidably receives a dispensing plunger that fits the passage, an elongate handle for the head, actuator means for the dispensing plunger, said instrument having an amalgam feed passage intersecting the dispensing passage, a feed plunger sliding in said feed passage and means for advancing said feed plunger; the improvement wherein said dispensing passage has an elongate planar rear wall and side walls that intersect said planer rear wall at an angle of about 90 degrees, said feed plunger having a planar front end face that forms a continuation of the planar rear wall of said dispensing passage when the feed plunger is fully advanced, said dispensing plunger having a planar rear surface that is laterally coextensive with said planar rear wall of said dispensing passage so that advance of said dispensing plunger, when the feed plunger is fully advanced, clears the passage intersection of amalgam, and wherein said dispensing head passage is formed to provide an elongate channel opening toward the front along a major portion of its length for cleaning, said channel having a length that at least equals that of said dispensing plunger, said dispensing plunger being detachably connected to said actuator means, and a detachable cover plate for closing the front of said channel, said dispensing plunger being removable from said head through the front of said channel.

4. A dental amalgam dispensing instrument of the type having a handle, a dispensing head on the handle and formed with a dispensing passage that slidably receives a dispensing plunger, actuator means for the dispensing plunger, an amalgam feed passage in said head intersecting the dispensing passage, a feed plunger having a forward portion sliding in said feed passage, and means for advancing the feed plunger; the improvement comprising means for detachably mounting said head on said handle, said feed passage being fully contained in the head, said feed plunger having a front end face that forms a continuation of the rear wall of said dispensing passage when the feed plunger is fully advanced so that advance of said dispensing plunger with the feed plunger fully advanced clears the passage intersection of amalgam, said plunger having a forward portion of uniform section that slides in the feed passage.

5. The instrument of claim 4; wherein said feed passage is a uniform section straight passage and said feed plunger is a straight rigid bar of uniform section along the portion thereof that slides in said feed passage.

6. The instrument of claim 5; comprising means for mounting said feed plunger in said handle, and spring means in the handle for advancing the feed plunger.

7. The instrument of claim 4; wherein the rear wall of said dispensing passage and the front end face of said feed plunger are both planar.

8. The instrument of claim 7; comprising stop means for limiting advance of said feed plunger to a position wherein its front end face is flush with the rear wall of said dispensing passage.

9. The instrument of claim 7; wherein both passages are of rectangular shape in cross-section.

10. A dental amalgam dispensing instrument of the type having an amalgam dispensing head formed with an amalgam dispensing passage, a dispensing plunger in said dispensing passage, means for actuating said dispensing plunger, said head having an amalgam feed passage intersecting said dispensing passage, a hollow handle, a separate feed plunger slidable in said handle and in said feed passage and spring means for advancing said feed plunger; the improvement comprising means for detachably securing the head to said handle, said feed passage being formed entirely in said head, said feed plunger being formed as a rigid straight bar projecting into the handle and stop means for slidably mounting and securing said feed plunger in said handle against the force of said spring means during withdrawal of the forward portion of the feed plunger from the feed passage in said head upon detachment of the head from the handle.

11. The instrument of claim 10; wherein said feed passage and plunger are of congruent rectangular shape in cross-section.

12. The instrument of claim 11; wherein said feed plunger is of uniform section along a major portion of its length, said stop means being on the rear portion of said feed plunger for limiting forward motion of the plunger, said stop being entirely disposed within said hollow handle.

13. The instrument of claim 10; wherein said amalgam dispensing passage has a flat rear wall, said feed plunger having a flat front end face, said stop means limiting advance of said feed plunger to a position wherein said front end face of the plunger is flush with the flat rear wall of said dispensing passage so that advance of said dispensing plunger clears the intersection of said passages of amalgam.

14. A dental amalgam dispensing instrument of the type having a handle, a dispensing head on the handle and formed with a dispensing passage that slidably receives a dispensing plunger, actuator means for the dispensing plunger, an amalgam feed passage in said head intersecting the dispensing passage, a feed plunger sliding in the feed passage, and means for advancing the feed plunger; the improvement comprises means for detachably mounting the rear portion of said head on the handle, said feed passage being fully contained in the head, the rear portion of said head having an amalgam loading section projecting rearwardly into said handle, said loading section being formed as an open side channel that forms a rearward continuation of the feed passage.

15. A dental amalgam dispensing instrument of the type having a handle, a dispensing head on the handle and formed with a dispensing passage that slidably receives a dispensing plunger, actuator means for the dispensing plunger, an amalgam feed passage in said head intersecting the dispensing passage, a feed plunger sliding in the feed passage, and means for advancing the feed plunger; the improvement wherein said dispensing passage is formed as a front opening channel having the same width as that of said dispensing plunger, said channel being at least as long as said dispensing plunger, means for detachably connecting said dispensing plunger to said actuator means so that the plunger can be removed from the head through the front of the channel, a cover plate for closing the front of said channel and means for detachably mounting said cover plate on the said head.

16. A dental amalgam dispensing instrument of the type having a dispensing head formed with a dispensing passage that slidably receives a dispensing plunger, a handle for the head, actuator means for the dispensing plunger, said instrument having an amalgam feed passage intersecting the dispensing passage, a feed plunger sliding in said feed passage and means for advancing said feed plunger; the improvement wherein said feed plunger has a front end face that is shaped to form a continuation of the rear wall of said dispensing passage when the feed plunger is fully advanced, so that advance of said dispensing plunger, when the feed plunger is fully advanced, clears the passage intersection of amalgam, said dispensing head passage being formed to provide an elongate channel opening toward the front for cleaning, keeper rib means on said head at each side of the channel, and a detachable cover plate for closing said channel, said cover plate having side retainer flanges for encompassing the rib means.

17. The instrument of claim 16; wherein the discharge portion of said head is formed with a socket for receiving one end of said cover plate.

18. A dental amalgam dispensing instrument of the type having a dispensing head formed with a dispensing passage that slidably receives a dispensing plunger, a handle for the head, actuator means for the dispensing plunger, said instrument having an amalgam feed passage intersecting the dispensing passage, a feed plunger sliding in said feed passage and means for advancing said feed plunger; the improvement wherein said feed plunger has a front end face that is shaped to form a continuation of the rear wall of said dispensing passage when the feed plunger is fully advanced, so that advance of said dispensing plunger when the feed plunger is fully advanced, clears the passage intersection of amalgam, means for detachably securing said dispensing head to said handle, said feed passage being wholly contained by said head, and means for mounting and retaining said feed plunger in said handle.

19. The instrument of claim 18; wherein said means for advancing the feed plunger comprises a coil compression spring mounted in the handle.

* * * * *